(12) United States Patent
Zones et al.

(10) Patent No.: US 9,468,917 B2
(45) Date of Patent: *Oct. 18, 2016

(54) PROCESSES USING MOLECULAR SIEVE SSZ-100

(71) Applicant: Chevron U.S.A. Inc., San Ramon, CA (US)

(72) Inventors: Stacey Ian Zones, San Francisco, CA (US); Dan Xie, Richmond, CA (US); Cong-Yan Chen, Kensington, CA (US); Ann Jia-Bao Liang, Walnut Creek, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 14/626,787

(22) Filed: Feb. 19, 2015

(65) Prior Publication Data
US 2015/0353368 A1 Dec. 10, 2015

Related U.S. Application Data

(60) Provisional application No. 62/007,878, filed on Jun. 4, 2014.

(51) Int. Cl.
| | |
|---|---|
| *B01J 29/70* | (2006.01) |
| *B01J 20/18* | (2006.01) |
| *B01D 53/94* | (2006.01) |
| *C07C 209/16* | (2006.01) |
| *B01D 71/02* | (2006.01) |
| *B01D 53/22* | (2006.01) |
| *C01B 39/48* | (2006.01) |
| *C07C 1/20* | (2006.01) |
| *B01D 67/00* | (2006.01) |
| *B01D 69/14* | (2006.01) |
| *B01J 37/02* | (2006.01) |
| *B01J 29/74* | (2006.01) |

(52) U.S. Cl.
CPC ............ *B01J 29/70* (2013.01); *B01D 53/228* (2013.01); *B01D 53/9413* (2013.01); *B01D 53/9486* (2013.01); *B01D 67/0051* (2013.01); *B01D 69/145* (2013.01); *B01D 69/147* (2013.01); *B01D 71/024* (2013.01); *B01D 71/025* (2013.01); *B01D 71/028* (2013.01); *B01J 20/18* (2013.01); *C01B 39/48* (2013.01); *C07C 1/20* (2013.01); *C07C 209/16* (2013.01); *B01D 2253/108* (2013.01); *B01D 2253/116* (2013.01); *B01D 2255/1021* (2013.01); *B01D 2255/1023* (2013.01); *B01D 2255/1025* (2013.01); *B01D 2255/2063* (2013.01); *B01D 2255/2073* (2013.01); *B01D 2255/2092* (2013.01); *B01D 2255/20738* (2013.01); *B01D 2255/20746* (2013.01); *B01D 2255/20753* (2013.01); *B01D 2255/20761* (2013.01); *B01D 2255/20784* (2013.01); *B01D 2255/20792* (2013.01); *B01D 2255/50* (2013.01); *B01D 2255/912* (2013.01); *B01D 2313/42* (2013.01); *B01D 2323/12* (2013.01); *B01D 2323/24* (2013.01); *B01J 29/74* (2013.01); *B01J 37/0246* (2013.01); *C07C 2529/70* (2013.01); *Y02P 30/42* (2015.11)

(58) Field of Classification Search
None
See application file for complete search history.

(56) References Cited

U.S. PATENT DOCUMENTS

| | | | |
|---|---|---|---|
| 4,910,006 A | 3/1990 | Zones et al. | |
| 7,648,694 B2 | 1/2010 | Burton, Jr. | |
| 7,837,978 B2 | 11/2010 | Burton, Jr. | |
| 2010/0260652 A1* | 10/2010 | Nakane | B01D 53/9413 423/213.2 |

FOREIGN PATENT DOCUMENTS

| | | |
|---|---|---|
| WO | 2010065319 | 6/2010 |
| WO | 2010088243 | 8/2010 |

OTHER PUBLICATIONS

S.I. Zones, M.M. Olmstead and D.S. Santilli "Guest/Host Relationships in the Synthesis of Large Pore Zeolite SSZ-26 from a Propellane Quaternary Ammonium Compound" J. Am. Chem. Soc. 1992, 114, 4195-4201.

PCT International Search Report, PCT/US2015/016526, mailed May 19, 2015.

* cited by examiner

*Primary Examiner* — Melvin C Mayes
*Assistant Examiner* — Sheng H Davis (57) ABSTRACT

This disclosure is directed to uses for a new crystalline molecular sieve designated SSZ-100. SSZ-100 is synthesized using a cationic nitrogen-containing organic compound having the following structure:

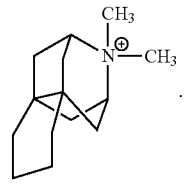

25 Claims, 3 Drawing Sheets

PROCESSES USING MOLECULAR SIEVE SSZ-100

TECHNICAL FIELD

This disclosure relates to a new crystalline molecular sieve designated SSZ-100, a method for preparing SSZ-100, and uses for SSZ-100.

BACKGROUND

Molecular sieve materials, both natural and synthetic, have been demonstrated in the past to be useful as adsorbents and to have catalytic properties for various types of hydrocarbon conversion reactions. Certain molecular sieves, such as zeolites, aluminophosphates, and mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Although many different crystalline molecular sieves have been discovered, there is a continuing need for new molecular sieves with desirable properties for gas separation and drying, hydrocarbon conversion reactions, and other applications. New molecular sieves can contain novel internal pore architectures, providing enhanced selectivities in these processes.

U.S. Pat. No. 4,910,006 discloses the synthesis of molecular sieve SSZ-26 using a hexamethyl[4.3.3.0] propellane-8,11-diammonium cation as structure directing agent ("SDA"). In the synthesis of this SDA from [4.3.3.0] propellane-8,11-dione, it was reported that a small amount of a mono-amine impurity was also produced in the reaction sequence. The mono-amine could be carried through all steps of the synthesis of the SDA without adversely affecting the synthesis of SSZ-26.

It has now been found that this reported mono-amine impurity is a mono quaternary ammonium compound, and when used as a structure directing agent, produces a unique molecular sieve material designated SSZ-100.

SUMMARY

The present disclosure is directed to a new family of molecular sieves with unique properties, referred to herein as "molecular sieve SSZ-100" or simply "SSZ-100."

In one aspect, there is provided a molecular sieve having a mole ratio of at least 10 of (1) at least one oxide of at least one tetravalent element to (2) optionally, one or more oxides selected from the group consisting of oxides of trivalent elements, pentavalent elements, and mixtures thereof, and having, in its as-synthesized form, the X-ray diffraction lines of Table 5. It should be noted that the phrase "mole ratio of at least 10" includes the case where there is no oxide (2), i.e., the mole ratio of oxide (1) to oxide (2) is infinity. In that case, the molecular sieve is comprised of essentially all of the oxide of the one or more tetravalent elements.

In another aspect, there is provided a method of preparing a crystalline molecular sieve by contacting under crystallization conditions (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; and (5) a cationic nitrogen-containing organic compound represented by the following structure:

In yet another aspect, there is provided a process for preparing a crystalline molecular sieve having, in its as-synthesized form, the X-ray diffraction lines of Table 5, by: (a) preparing a reaction mixture containing (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) water; and (6) a cationic nitrogen-containing organic compound represented by the following structure:

and (b) subjecting the reaction mixture to crystallization conditions sufficient to form crystals of the molecular sieve.

The present disclosure also provides processes using SSZ-100 molecular sieves having a composition, as-synthesized and in the anhydrous state, in terms of mole ratios, as follows:

|  | Broad | Exemplary |
| --- | --- | --- |
| $TO_2/X_2O_b$ | ≥10 | 10 to 100 |
| $Q/TO_2$ | 0.02 to 0.10 | 0.02 to 0.10 |
| $M/TO_2$ | 0.02 to 0.15 | 0.02 to 0.15 | wherein: (1) T is selected from the group consisting of tetravalent elements from Groups 4-14 of the Periodic Table, and mixtures thereof; (2) X is selected from the group consisting of trivalent and pentavalent elements from Groups 3-13 of the Periodic Table, and mixtures thereof; (3) stoichiometric variable b equals the valence state of compositional variable X (e.g., when X is trivalent, b=3; when X is pentavalent, b=5); (4) M is selected from the group consisting of elements from Groups 1 and 2 of the Periodic Table; and (5) Q is a cationic nitrogen-containing organic compound represented by the following structure:

DETAILED DESCRIPTION

Introduction

The term "molecular sieve" includes (a) intermediate and (b) final or target molecular sieves and molecular sieves produced by (1) direct synthesis or (2) post-crystallization treatment (secondary synthesis). Secondary synthesis techniques allow for the synthesis of a target material from an intermediate material by heteroatom lattice substitution or other techniques. For example, an aluminosilicate can be synthesized from an intermediate borosilicate by post-crystallization heteroatom lattice substitution of the boron for aluminum. Such techniques are known, for example as described in U.S. Pat. No. 6,790,433.

As used herein, the numbering scheme for the Periodic Table Groups is as disclosed in *Chem. Eng. News,* 63(5), 27 (1985).

In preparing SSZ-100, a cationic nitrogen-containing organic compound represented by the flowing structure (1) is used as the structure directing agent ("SDA"), also known as a crystallization template:

(1)

The SDA cation is associated with anions which can be any anion that is not detrimental to the formation of SSZ-100. Representative anions include elements from Group 17 of the Periodic Table (e.g., fluoride, chloride, bromide and iodide), hydroxide, acetate, sulfate, tetrafluoroborate, carboxylate, and the like.

Reaction Mixture

In general, molecular sieve SSZ-100 is prepared by: (a) preparing a reaction mixture containing (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) water; and (6) a cationic nitrogen-containing organic compound represented by the following structure and (b) subjecting the reaction mixture to crystallization conditions sufficient to form crystals of the molecular sieve.

The composition of the reaction mixture from which the molecular sieve is formed, in terms of mole ratios, is identified in Table 1 below, wherein compositional variables T, X, M, and Q and stoichiometric variable b are as described herein above.

TABLE 1

| Components | Broad | Exemplary |
|---|---|---|
| $TO_2/X_2O_b$ | ≥10 | 10 to 100 |
| $M/TO_2$ | 0.05 to 0.50 | 0.15 to 0.30 |
| $Q/TO_2$ | 0.05 to 0.50 | 0.05 to 0.25 |
| $OH/TO_2$ | 0.10 to 1.0 | 0.10 to 0.50 |
| $H_2O/TO_2$ | 15 to 300 | 25 to 60 |

In one sub-embodiment, the composition of the reaction mixture from which SSZ-100 is formed, in terms of mole ratios, is identified in Table 2 below, wherein compositional variables M and Q are as described herein above.

TABLE 2

| Components | Broad | Exemplary |
|---|---|---|
| $SiO_2/Al_2O_3$ | ≥10 | 10 to 100 |
| $M/SiO_2$ | 0.05 to 0.50 | 0.15 to 0.30 |
| $Q/SiO_2$ | 0.05 to 0.50 | 0.05 to 0.25 |
| $OH/SiO_2$ | 0.10 to 1.0 | 0.10 to 0.50 |
| $H_2O/SiO_2$ | 15 to 300 | 25 to 60 |

As noted above, for each embodiment described herein, T is selected from the group consisting of tetravalent elements from Groups 4-14 of the Periodic Table. In one sub-embodiment, T is selected from the group consisting of silicon (Si), germanium (Ge), titanium (Ti), and mixtures thereof. In another sub-embodiment, T is selected from the group consisting of Si, Ge, and mixtures thereof. In one sub-embodiment, T is Si. Sources of elements selected for compositional variable T include oxides, hydroxides, acetates, oxalates, ammonium salts and sulfates of the element(s) selected for T. In one sub-embodiment, each source(s) of the element(s) selected for composition variable T is an oxide. Where T is Si, sources useful for Si include fumed silica, precipitated silicates, silica hydrogel, silicic acid, colloidal silica, tetra-alkyl orthosilicates (e.g., tetraethyl orthosilicate), and silica hydroxides. Sources useful herein for Ge include germanium oxide and germanium ethoxide.

For each embodiment described herein, X is selected from the group consisting of trivalent and pentavalent elements from Groups 3-13 of the Periodic Table. In one sub-embodiment, X is selected from the group consisting of boron (B), aluminum (Al), gallium (Ga), indium (In), iron (Fe), and mixtures thereof. In another sub-embodiment, X is selected from the group consisting of B, Al, Ga, In, and mixtures thereof. In one sub-embodiment X is Al. Sources of elements selected for compositional variable X include oxides, hydroxides, acetates, oxalates, ammonium salts and sulfates of the element(s) selected for X. Where X is Al, sources useful for Al include aluminates, alumina, and aluminum compounds such as $AlCl_3$, $Al_2(SO_4)_3$, $Al(OH)_3$, kaolin clays, and other zeolites. An example of the source of aluminum oxide is LZ-210 zeolite (a type of Y zeolite). Boron, gallium, indium, titanium, and iron can be added in forms corresponding to their aluminum and silicon counterparts.

As described herein above, for each embodiment described herein, the reaction mixture can be formed using at least one source of an element selected from Groups 1 and 2 of the Periodic Table (referred to herein as M). In one sub-embodiment, the reaction mixture is formed using a source of an element from Group 1 of the Periodic Table. In another sub-embodiment, the reaction mixture is formed using a source of sodium (Na). Any M-containing compound which is not detrimental to the crystallization process is suitable. Sources for such Groups 1 and 2 elements include oxides, hydroxides, nitrates, sulfates, halides, oxalates, citrates and acetates thereof.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

In practice, the molecular sieve is prepared by: (a) preparing a reaction mixture as described herein above; and (b) subjecting the reaction mixture to crystallization conditions sufficient to form crystals of the molecular sieve.

The reaction mixture is maintained at an elevated temperature until the crystals of the molecular sieve are formed. The hydrothermal crystallization is usually conducted under pressure, and usually in an autoclave so that the reaction mixture is subject to autogenous pressure, at a temperature between 125° C. and 200° C.

The reaction mixture can be subjected to mild stirring or agitation during the crystallization step. It will be understood the skilled artisan that the molecular sieves described herein can contain impurities, such as amorphous materials, unit cells having framework topologies which do not coincide with the molecular sieve, and/or other impurities (e.g., organic hydrocarbons).

During the hydrothermal crystallization step, the molecular sieve crystals can be allowed to nucleate spontaneously from the reaction mixture. The use of crystals of the molecular sieve as seed material can be advantageous in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 1% and 10% of the weight of the source for compositional variable T used in the reaction mixture.

Once the molecular sieve crystals have formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

The molecular sieve can be used as-synthesized, but typically will be thermally treated (calcined). The term "as-synthesized" refers to the molecular sieve in its form after crystallization, prior to removal of the SDA cation. The SDA can be removed by thermal treatment (e.g., calcination), preferably in an oxidative atmosphere (e.g., air, gas with an oxygen partial pressure of greater than 0 kPa) at a temperature readily determinable by the skilled artisan sufficient to remove the SDA from the molecular sieve. The SDA can also be removed by photolysis techniques (e.g., exposing the SDA-containing molecular sieve product to light or electromagnetic radiation that has a wavelength shorter than visible light under conditions sufficient to selectively remove the organic compound from the molecular sieve) as described in U.S. Pat. No. 6,960,327.

The molecular sieve can subsequently be calcined in steam, air or inert gas at temperatures ranging from 200° C. to 800° C. for periods of time ranging from 1 to 48 hours, or more. Usually, it is desirable to remove the extra-framework cation (e.g., $Na^+$) by ion exchange and replace it with hydrogen, ammonium, or any desired metal-ion.

Where the molecular sieve formed is an intermediate material, the target molecular sieve can be achieved using post-synthesis techniques such as heteroatom lattice substitution techniques. The target molecular sieve can also be achieved by removing heteroatoms from the lattice by known techniques such as acid leaching.

The molecular sieve made from the process disclosed herein can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying or dried (or partially dried) and then extruded.

The molecular sieve can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. Nos. 4,910,006 and 5,316,753.

Characterization of the Molecular Sieve

Molecular sieves made by the process disclosed herein have a composition, as-synthesized and in the anhydrous state, as described in Table 3 (in terms of mole ratios), wherein compositional variables T, X, Q and M and stoichiometric variable b are as described herein above:

TABLE 3

|  | Broad | Exemplary |
| --- | --- | --- |
| $TO_2/X_2O_b$ | ≥10 | 10 to 100 |
| $Q/TO_2$ | 0.02 to 0.10 | 0.02 to 0.10 |
| $M/TO_2$ | 0.02 to 0.15 | 0.02 to 0.15 |

In one sub-embodiment, the molecular sieves made by the process disclosed herein have a composition, as-synthesized and in the anhydrous state, as described in Table 4 (in terms of mole ratios), wherein compositional variables Q and M are as described herein above:

TABLE 4

|  | Broad | Exemplary |
|---|---|---|
| $SiO_2/Al_2O_3$ | ≥10 | 10 to 100 |
| $Q/SiO_2$ | 0.02 to 0.10 | 0.02 to 0.10 |
| $M/SiO_2$ | 0.02 to 0.15 | 0.02 to 0.15 |

Molecular sieves synthesized by the process disclosed herein are characterized by their XRD pattern. The X-ray diffraction pattern lines of Table 5 are representative of as-synthesized SSZ-100 made in accordance with this disclosure. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

TABLE 5

Characteristic Peaks for As-Synthesized SSZ-100

| 2-Theta[a] | d-Spacing, nm | Relative Intensity[b] |
|---|---|---|
| 8.50 | 1.039 | M |
| 8.99 | 0.983 | S |
| 9.99 | 0.885 | M |
| 12.43 | 0.712 | W |
| 14.06 | 0.630 | W |
| 15.88 | 0.558 | VS |
| 17.68 | 0.501 | VS |
| 18.56 | 0.478 | VS |
| 19.35 | 0.458 | VS |
| 19.94 | 0.445 | VS |
| 20.87 | 0.425 | W |
| 22.80 | 0.390 | M |
| 23.36 | 0.381 | W |
| 24.74 | 0.360 | M |
| 24.99 | 0.356 | VS |

[a]±0.20
[b]The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The X-ray diffraction pattern lines of Table 6 are representative of calcined SSZ-100 made in accordance with this disclosure.

TABLE 6

Characteristic Peaks for Calcined SSZ-100

| 2-Theta[a] | d-Spacing, nm | Relative Intensity[b] |
|---|---|---|
| 8.48 | 1.041 | VS |
| 8.98 | 0.984 | VS |
| 10.04 | 0.880 | S |
| 12.38 | 0.714 | W |
| 14.17 | 0.625 | W |
| 15.85 | 0.559 | S |
| 17.07 | 0.519 | W |
| 17.64 | 0.503 | M |
| 18.68 | 0.475 | S |
| 19.44 | 0.456 | W |
| 19.78 | 0.449 | M |
| 19.98 | 0.444 | S |
| 20.22 | 0.439 | W |
| 21.30 | 0.417 | W |
| 22.80 | 0.390 | M |
| 23.06 | 0.385 | M |
| 24.29 | 0.366 | W |
| 24.99 | 0.356 | VS |

[a]±0.20
[b]The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuKα radiation. The peak heights and the positions, as a function of 2θ where θ is the Bragg angle, were read from the relative intensities of the peaks (adjusting for background), and d, the interplanar spacing corresponding to the recorded lines, can be calculated.

Processes Using SSZ-100

SSZ-100 is useful as an adsorbent for gas separations. SSZ-100 can also be used as a catalyst for converting oxygenates (e.g., methanol) to olefins and for making small amines. SSZ-100 can be used to reduce oxides of nitrogen in a gas streams, such as automobile exhaust. SSZ-100 can also be used to as a cold start hydrocarbon trap in combustion engine pollution control systems. SSZ-100 is particularly useful for trapping $C_3$ fragments.

Gas Separation

SSZ-100 can be used to separate gases. For example, it can be used to separate carbon dioxide from natural gas. Typically, the molecular sieve is used as a component in a membrane that is used to separate the gases. Examples of such membranes are disclosed in U.S. Pat. No. 6,508,860.

Oxygenate Conversion

The disclosed herein comprises a process for catalytic conversion of a feedstock comprising one or more oxygenates comprising alcohols and ethers to a hydrocarbon product containing light olefins, i.e., $C_2$, $C_3$ and/or $C_4$ olefins. The feedstock is contacted with SSZ-100 at effective process conditions to produce light olefins. The term "oxygenate" as used herein designates compounds such as alcohols, ethers, and carbonyl compounds (e.g., aldehydes, ketones, carboxylic acids). The oxygenate can contain from 1 to 10 carbon atoms, e.g., from 1 to 4 carbon atoms. The representative oxygenates include lower straight chained branched alcohols, and their unsaturated counterparts. Particularly suitable oxygenate compounds are methanol, dimethyl ether, and mixtures thereof.

The process disclosed can be conducted in the presence of one or more diluents which can be present in the oxygenate feed in an amount of from 1 to 99 mole %, based on the total number of moles of all feed and diluent components. Diluents include helium, argon, nitrogen, carbon monoxide, carbon dioxide, hydrogen, water, paraffins, hydrocarbons (such as methane and the like), aromatic compounds, or mixtures thereof. U.S. Pat. Nos. 4,677,242; 4,861,938; and 4,677,242 emphasize the use of a diluent to maintain catalyst selectivity toward the production of light olefins, particularly ethylene.

The oxygenate conversion is desirably conducted in the vapor phase such that the oxygenate feedstock is contacted in a vapor phase in a reaction zone with SSZ-100 at effective process conditions to produce hydrocarbons, i.e., an effective temperature, pressure, WHSV and, optionally, an effective amount of diluent. The process is conducted for a period of time sufficient to produce the desired light olefins. In general, the residence time employed to produce the desired product can vary from seconds to a number of hours. It will be readily appreciated that the residence time will be determined to a significant extent by the reaction temperature, the molecular sieve catalyst, the WHSV, the phase (liquid or vapor) and process design characteristics. The oxygenate feedstock flow rate affects olefin production. Increasing the feedstock flow rate increases WHSV and enhances the formation of olefin production relative to paraffin production. However, the enhanced olefin production relative to paraffin production is offset by a diminished conversion of oxygenate to hydrocarbons.

Light olefin products will form, although not necessarily in optimum amounts, at a wide range of pressures, including but not limited to autogenous pressures and pressures in the range from 0.1 kPa to 10 MPa. Conveniently, the pressure can be in the range from 7 kPa to 5 MPa, e.g., from 50 kPa to 1 MPa. The foregoing pressures are exclusive of diluents, if any are present, and refer to the partial pressure of the feedstock as it relates to oxygenate compounds and/or mixtures thereof. Lower and upper extremes of pressure can adversely affect selectivity, conversion, coking rate, and/or reaction rate; however, light olefins such as ethylene and/or propylene still may form.

The temperature which can be employed in the oxygenate conversion process can vary over a wide range depending, at least in part, on the molecular sieve catalyst. In general, the process can be conducted at an effective temperature of from 200° C. to 700° C. At the lower ends of the temperature range, and thus generally at a lower rate of reaction, the formation of the desired light olefins can become low. At the upper ends of the range, the process may not form an optimum amount of light olefins and catalyst deactivation can be rapid.

The molecular sieve catalyst can be incorporated into solid particles in which the catalyst is present in an amount effective to promote the desired conversion of oxygenates to light olefins. In one aspect, the solid particles comprise a catalytically effective amount of the catalyst and at least one matrix material selected from the group consisting of binder materials, filler materials and mixtures thereof to provide a desired property or properties, e.g., desired catalyst dilution, mechanical strength and the like to the solid particles. Such matrix materials are often, to some extent, porous in nature and can or cannot be effective to promote the desired reaction. Filler and binder materials include, for example, synthetic and naturally occurring substances such as metal oxides, clays, silicas, aluminas, silica-aluminas, silica-magnesias, silica-zirconias, silica-thorias and the like. If matrix materials are included in the catalyst composition, the molecular sieve desirably comprises from 1 to 99 wt. % (e.g., from 5 to 90 wt. % or from 10 to 80 wt. %) of the total composition.

Synthesis of Amines

SSZ-100 can be used in a catalyst to prepare methylamine or dimethylamine. Dimethylamine is generally prepared in industrial quantities by continuous reaction of methanol (and/or dimethyl ether) and ammonia in the presence of a silica-alumina catalyst. The reactants are typically combined in the vapor phase, at temperatures of from 300° C. to 500° C., and at elevated pressures. Such a process is disclosed in U.S. Pat. No. 4,737,592.

The catalyst is used in its acid form. Acid forms of molecular sieves can be prepared by a variety of techniques. Desirably, the molecular sieve used to prepare dimethylamine will be in the hydrogen form, or have an alkali or alkaline earth metal, such as Na, K, Rb, or Cs, ion-exchanged into it.

The process disclosed herein involves reacting methanol, dimethyl ether, or a mixture thereof and ammonia in amounts sufficient to provide a carbon/nitrogen (C/N) ratio of from 0.2 to 1.5, e.g., from 0.5 to 1.2. The reaction is conducted at a temperature of from 250° C. to 450° C., e.g., from 300° C. to 400° C. Reaction pressures can vary from 7 to 7000 kPa, e.g., from 70 to 3000 kPa. A methanol and/or dimethyl ether space time of from 0.01 to 80 $h^{-1}$ (e.g., from 0.10 to 1.5 $h^{-1}$) is typically used. This space time is calculated as the mass of catalyst divided by the mass flow rate of methanol/dimethyl ether introduced into the reactor.

Reduction of Oxides of Nitrogen

SSZ-100 can be used for the catalytic reduction of the oxides of nitrogen in a gas stream. Typically, the gas stream also contains oxygen, often a stoichiometric excess thereof. Also, the molecular sieve can contain a metal or metal ions within or on it which are capable of catalyzing the reduction of the nitrogen oxides. Examples of such metals or metal ions include lanthanum, chromium, manganese, iron, cobalt, rhodium, nickel, palladium, platinum, copper, zinc, and mixtures thereof.

One example of such a process for the catalytic reduction of oxides of nitrogen in the presence of a zeolite is disclosed in U.S. Pat. No. 4,297,328. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

Treatment of Engine Exhaust (Cold Start Emissions)

Gaseous waste products resulting from the combustion of hydrocarbon fuels, such as gasoline and fuel oils, comprise carbon monoxide, hydrocarbons and nitrogen oxides as products of combustion or incomplete combustion, and can pose a serious health problem with respect to pollution of the atmosphere. While exhaust gases from other carbonaceous fuel-burning sources, such as stationary engines, industrial furnaces, etc., contribute substantially to air pollution, the exhaust gases from automotive engines are a principal source of pollution. Because of these concerns, the U.S. Environmental Protection Agency has promulgated strict controls on the amounts of carbon monoxide, hydrocarbons and nitrogen oxides which automobiles can emit. The implementation of these controls has resulted in the use of catalytic converters to reduce the amount of pollutants emitted from automobiles.

In order to achieve the simultaneous conversion of carbon monoxide, hydrocarbon and nitrogen oxide pollutants, it has become the practice to employ catalysts in conjunction with air-to-fuel ratio control means which functions in response to a feedback signal from an oxygen sensor in the engine exhaust system. Although these three component control catalysts work quite well after they have reached operating temperature of about 300° C., at lower temperatures they are not able to convert substantial amounts of the pollutants. What this means is that when an engine and in particular an automobile engine is started up, the three component control catalyst is not able to convert the hydrocarbons and other pollutants to innocuous compounds.

Adsorbent beds have been used to adsorb the hydrocarbons during the cold start portion of the engine. Although the process typically will be used with hydrocarbon fuels, the present disclosure can also be used to treat exhaust streams from alcohol-fueled engines. The adsorbent bed is typically placed immediately before the catalyst. Thus, the exhaust stream is first flowed through the adsorbent bed and then through the catalyst. The adsorbent bed preferentially adsorbs hydrocarbons over water under the conditions present in the exhaust stream. After a certain amount of time, the adsorbent bed has reached a temperature (typically about 150° C.) at which the bed is no longer able to remove hydrocarbons from the exhaust stream. That is, hydrocarbons are actually desorbed from the adsorbent bed instead of being adsorbed. This regenerates the adsorbent bed so that it can adsorb hydrocarbons during a subsequent cold start. The use of adsorbent beds to minimize hydrocarbon emissions during a cold start engine operation is known in the art. See, for example, U.S. Pat. Nos. 2,942,932; 3,699,683; and 5,078,979.

As stated, this disclosure generally relates to a process for treating an engine exhaust stream and, in particular, to a process for minimizing emissions during the cold start operation of an engine. The engine consists of any internal or external combustion engine which generates an exhaust gas stream containing noxious components or pollutants including unburned or thermally degraded hydrocarbons or similar organics. Other noxious components usually present in the exhaust gas include nitrogen oxides and carbon monoxide. The engine can be fueled by a hydrocarbon fuel. As used herein, the term "hydrocarbon fuel" includes hydrocarbons, alcohols and mixtures thereof. Examples of hydrocarbons which can be used to fuel the engine are the mixtures of hydrocarbons which make up gasoline or diesel fuel. The alcohols which can be used to fuel engines include ethanol and methanol. Mixtures of alcohols and mixtures of alcohols and hydrocarbons can also be used. The engine can be a jet engine, gas turbine, internal combustion engine, such as an automobile, truck or bus engine, a diesel engine or the like. The process of this disclosure is particularly suited for an internal combustion engine mounted in an automobile.

When the engine is started up, it produces a relatively high concentration of hydrocarbons in the engine exhaust gas stream as well as other pollutants. Pollutants will be used herein to collectively refer to any unburned fuel components and combustion byproducts found in the exhaust stream. For example, when the fuel is a hydrocarbon fuel, hydrocarbons, nitrogen oxides, carbon monoxide and other combustion byproducts will be found in the engine exhaust gas stream. The temperature of this engine exhaust stream is relatively cool, generally below 500° C. and typically in the range of from 200° C. to 400° C. This engine exhaust stream has the above characteristics during the initial period of engine operation, typically for the first 30 to 120 seconds after startup of a cold engine. The engine exhaust stream will typically contain from 500 to 1000 ppm hydrocarbons by volume.

In one embodiment, the engine exhaust gas stream which is to be treated is flowed over a combination of molecular sieves which preferentially adsorbs the hydrocarbons over water to provide a first exhaust stream, and flowing the first exhaust gas stream over a catalyst to convert any residual hydrocarbons and other pollutants contained in the first exhaust gas stream to innocuous products and provide a treated exhaust stream and discharging the treated exhaust stream into the atmosphere. The combination of molecular sieves includes SSZ-100 in combination with: (1) a small pore crystalline molecular sieve or mixture of molecular sieves having pores no larger than 8-membered rings selected from the group consisting of SSZ-13, SSZ-16, SSZ-36, SSZ-39, SSZ-50, SSZ-52 and SSZ-73 and having a mote ratio of at least 10 of (a) at least one oxide of at least one tetravalent element to (b) one or more oxides selected from the group consisting of oxides of trivalent elements, pentavalent elements, and mixtures thereof and/or (2) a large pore crystalline molecular sieve having pores at least as large as 10-membered rings selected from the group consisting of SSZ-26, SSZ-33, SSZ-64, zeolite Beta, CIT-1, CIT-6 and ITQ-4 and having a mole ratio of at least 10 of (a) at least one oxide of at least one tetravalent element to (b) one or more oxides selected from the group consisting of oxides of trivalent elements, pentavalent elements, and mixtures thereof.

The engine exhaust gas stream which is to be treated is flowed over a molecular sieve bed comprising molecular sieve SSZ-100 as a first exhaust stream. The first exhaust stream which is discharged from the molecular sieve bed is now flowed over a catalyst to convert the pollutants contained in the first exhaust stream to innocuous components and provide a treated exhaust stream which is discharged into the atmosphere. It is understood that prior to discharge into the atmosphere, the treated exhaust stream can be flowed through a muffler or other sound reduction apparatus well known in the art.

The catalyst which is used to convert the pollutants to innocuous components is usually referred to in the art as a three-component control catalyst because it can simultaneously oxidize any residual hydrocarbons present in the first exhaust stream to carbon dioxide and water, oxidize any residual carbon monoxide to carbon dioxide and reduce any residual nitric oxide to nitrogen and oxygen. In some cases the catalyst cannot be required to convert nitric oxide to nitrogen and oxygen, e.g., when an alcohol is used as the fuel. In this case the catalyst is called an oxidation catalyst. Because of the relatively low temperature of the engine exhaust stream and the first exhaust stream, this catalyst does not function at a very high efficiency, thereby necessitating the molecular sieve bed.

When the molecular sieve bed reaches a sufficient temperature, typically from 150° C. to 200° C., the pollutants which are adsorbed in the bed begin to desorb and are carried by the first exhaust stream over the catalyst. At this point the catalyst has reached its operating temperature and is therefore capable of fully converting the pollutants to innocuous components.

The adsorbent bed used in this disclosure can be conveniently employed in particulate form or the adsorbent can be deposited onto a solid monolithic carrier. When particulate form is desired, the adsorbent can be formed into shapes such as pills, pellets, granules, rings, spheres, etc. In the employment of a monolithic form, it is usually most convenient to employ the adsorbent as a thin film or coating deposited on an inert carrier material which provides the structural support for the adsorbent. The inert carrier material can be any refractory material such as ceramic or metallic materials. It is desirable that the carrier material be unreactive with the adsorbent and not be degraded by the gas to which it is exposed. Examples of suitable ceramic materials include sillimanite, petalite, cordierite, mullite, zircon, zircon mullite, spondumene, alumina-titanate, etc. Additionally, metallic materials which are within the scope of this disclosure include metals and alloys as disclosed in U.S. Pat. No. 3,920,583 which are oxidation resistant and are otherwise capable of withstanding high temperatures.

The carrier material can best be utilized in any rigid unitary configuration which provides a plurality of pores or channels extending in the direction of gas flow. The configuration can be a honeycomb configuration. The honeycomb structure can be used advantageously in either unitary form, or as an arrangement of multiple modules. The honeycomb structure is usually oriented such that gas flow is generally in the same direction as the cells or channels of the honeycomb structure. For a more detailed discussion of monolithic structures, refer to U.S. Pat. Nos. 3,767,453 and 3,785,998.

The molecular sieve is deposited onto the carrier by any convenient way well known in the art. A desirable method involves preparing a slurry using the molecular sieve and coating the monolithic honeycomb carrier with the slurry. The slurry can be prepared by means known in the art such as combining the appropriate amount of the molecular sieve and a binder with water. This mixture is then blended by using means such as sonication, milling, etc. This slurry is used to coat a monolithic honeycomb by dipping the honeycomb into the slurry, removing the excess slurry by draining or blowing out the channels, and heating to about 100° C. If the desired loading of molecular sieve is not achieved, the above process can be repeated as many times as required to achieve the desired loading.

Instead of depositing the molecular sieve onto a monolithic honeycomb structure, the molecular sieve can be formed into a monolithic honeycomb structure by means known in the art.

The adsorbent can optionally contain one or more catalytic metals dispersed thereon. The metals which can be dispersed on the adsorbent are the noble metals which consist of ruthenium, rhodium, palladium, platinum, and mixtures thereof. The desired noble metal can be deposited onto the adsorbent, which acts as a support, in any suitable manner well known in the art. One example of a method of dispersing the noble metal onto the adsorbent support involves impregnating the adsorbent support with an aqueous solution of a decomposable compound of the desired noble metal or metals, drying the adsorbent which has the noble metal compound dispersed on it and then calcining in air at a temperature of 400° C. to 500° C. for a time of from 1 to 4 hours. By decomposable compound is meant a compound which upon heating in air gives the metal or metal oxide. Examples of the decomposable compounds which can be used are set forth in U.S. Pat. No. 4,791,091. Examples of decomposable compounds are chloroplatinic acid, rhodium trichloride, chloropalladic acid, hexachloroiridate(IV) acid and hexachlororuthenate(IV). It is typical that the noble metal be present in an amount ranging from 0.01 to 4 wt. % of the adsorbent support. Specifically, in the case of platinum and palladium the range is from 0.1 to 4 wt. %, while in the case of rhodium and ruthenium the range is from 0.01 to 2 wt. %.

These catalytic metals are capable of oxidizing the hydrocarbon and carbon monoxide and reducing the nitric oxide components to innocuous products. Accordingly, the adsorbent bed can act both as an adsorbent and as a catalyst.

The catalyst which is used in this disclosure is selected from any three component control or oxidation catalyst well known in the art. Examples of catalysts are those described in U.S. Pat. Nos. 4,528,279; 4,760,044; 4,791,091; 4,868,148; and 4,868,149. Desirable catalysts well known in the art are those that contain platinum and rhodium and optionally palladium, while oxidation catalysts usually do not contain rhodium. Oxidation catalysts usually contain platinum and/or palladium metal. These catalysts can also contain promoters and stabilizers such as barium, cerium, lanthanum, nickel, and iron. The noble metals promoters and stabilizers are usually deposited on a support such as alumina, silica, titania, zirconia, alumino silicates, and mixtures thereof with alumina being desirable. The catalyst can be conveniently employed in particulate form or the catalytic composite can be deposited on a solid monolithic carrier with a monolithic carrier being desirable. The particulate form and monolithic form of the catalyst are prepared as described for the adsorbent above. The molecular sieve used in the adsorbent bed is SSZ-100.

EXAMPLES

The following illustrative examples are intended to be non-limiting.

Example 1

Synthesis of SDA

The SDA was prepared according to Zones et al., *J. Am. Chem. Soc.* 1992, 114, 4195-4201. The SDA can be isolated as eluting faster off a column than the diquaternary SDA used for synthesizing SSZ-26. The iodide product was then hydroxide-exchanged by dissolving the solid in a 5-fold mass excess of water, adding a 2.5-fold mass excess of AG® 1-X8 anion exchange resin (Bio-Rad Laboratories), and allowing the ion-exchange to occur overnight. The solution was filtered and the resin was washed with another $\frac{1}{4}^{th}$ proportion (relative to the start) of water. The combined aqueous fractions were titrated with 0.1N HCl to determine the hydroxide concentration.

Figure 1:
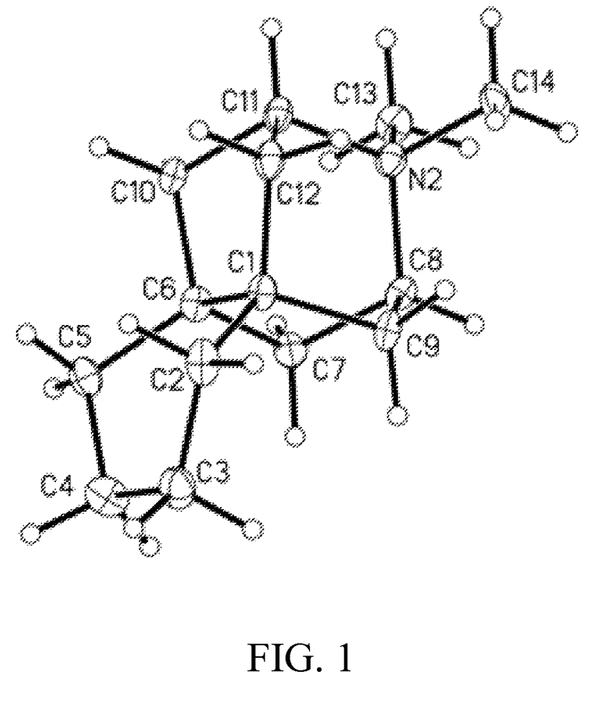
FIG. 1 depicts the structure of the SDA prepared in Example 1 drawn with 30% thermal ellipsoids as determined by single-crystal X-ray diffraction.

The molecular structure of the SDA was determined by single-crystal X-ray diffraction using standard techniques and is depicted in FIG. 1.

Example 2

Synthesis of SSZ-100

CAB-O-SIL® M5 fumed silica (Cabot Corp.), a FAU zeolite ($SiO_2/Al_2O_3$ mole ratio=5), a hydroxide solution of the SDA synthesized per Example 1, 1 N NaOH, and deionized were mixed together in a Teflon liner. The composition of the reaction mixture, in terms of mole ratios, is reported in Table 7.

TABLE 7

| Reaction Mixture Composition | |
|---|---|
| $SiO_2/Al_2O_3$ | 35 |
| $Q/SiO_2$ | 0.20 |
| $OH/SiO_2$ | 0.15 |
| $H_2O/SiO_2$ | 30 |

The Teflon liner was then capped and sealed within a steel Parr autoclave. The autoclave was placed on a spit within a convection oven at 160° C. The autoclave was tumbled at 43 rpm for a week in the heated oven. The autoclave was then removed and allowed to cool to room temperature. The solids were then recovered by filtration and washed thoroughly with deionized water. The solids were allowed to dry at room temperature.

Figure 2:
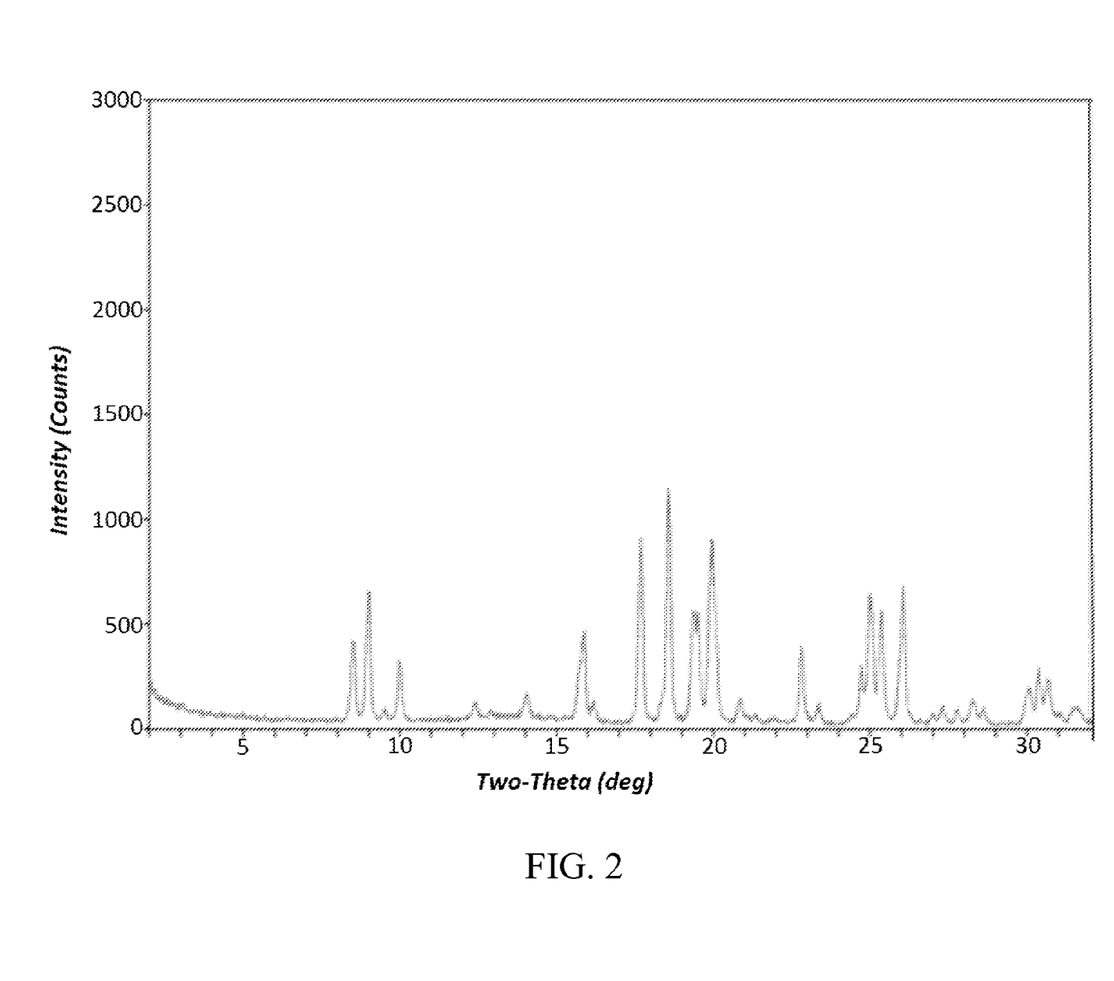
FIG. 2 is a powder XRD pattern of the as-synthesized molecular sieve prepared in Example 2.

The powder XRD pattern of the resulting product is shown in FIG. 2.

Elemental analysis indicated the product contained 33.2% Si and 2.67% Al.

Example 3

Calcination of SSZ-100

Figure 3:
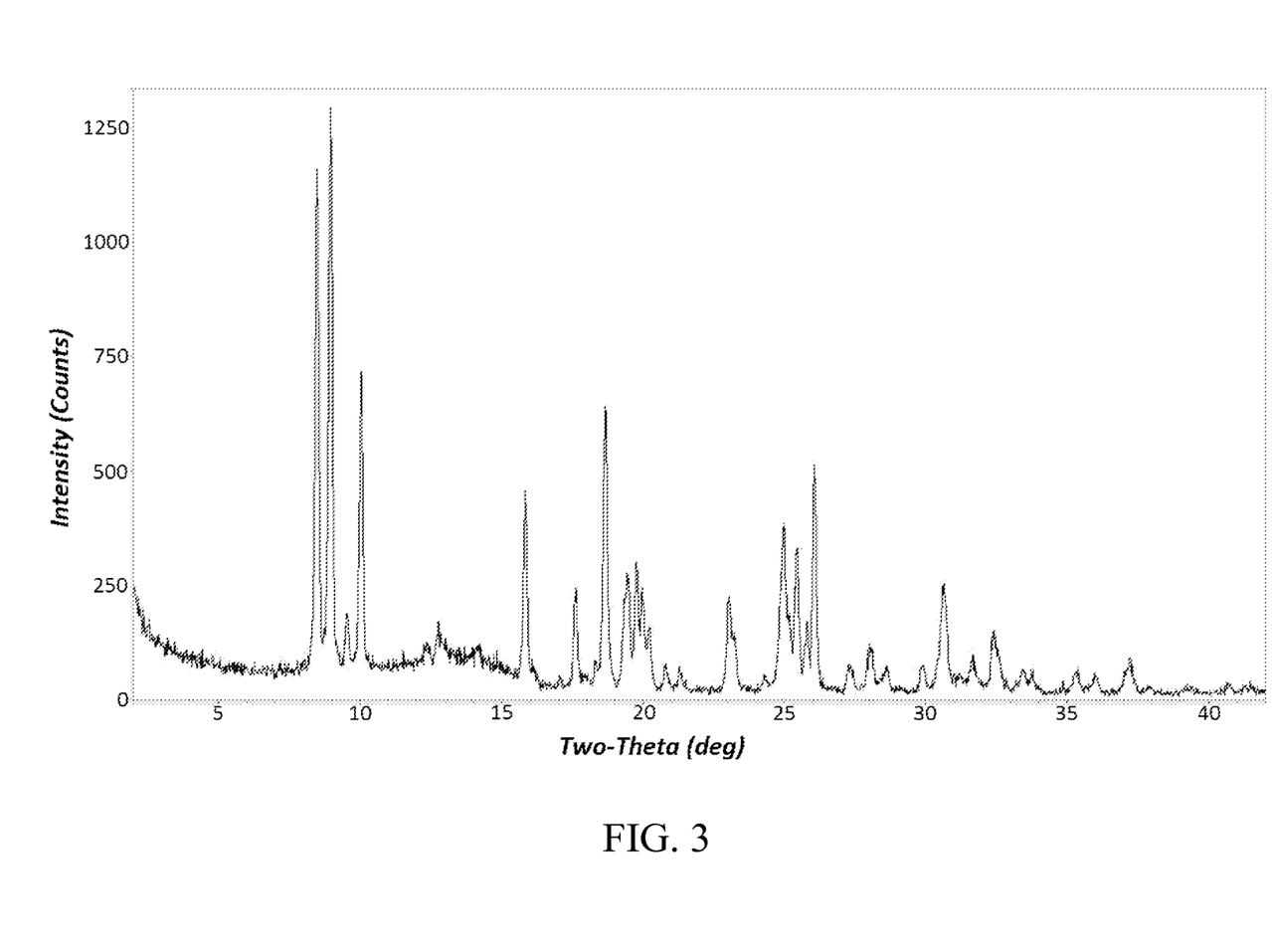
FIG. 3 is a powder XRD pattern of the calcined molecular sieve prepared in Example 3.

The resulting product was calcined inside a muffle furnace under a flow of air heated to 595° C. at a rate of 1° C./minute and held at 595° C. for 5 hours, cooled and then analyzed by powder XRD. The powder XRD pattern of the resulting product is shown in FIG. 3. The powder XRD pattern indicates that the material remains stable after calcination to remove the organic SDA.

Example 3

Micropore Volume Analysis

Calcined SSZ-100 was subjected to a surface area and micropore volume analysis using $N_2$ as adsorbate and via the BET method. The zeolite exhibited a considerable void volume with a micropore volume of 0.22 cm$^3$/g. This is consistent with the SDA filling about 18 wt. % for the as-synthesized SSZ-100.

No n-hexane uptake for calcined SSZ-100 was observed at room temperature indicating that SSZ-100 is a small pore molecular sieve (i.e., a molecular sieve having a pore size of from 3 Å to less than 5.0 Å).

Example 4

Ammonium-Ion Exchange of SSZ-100

The Na$^+$ form of calcined SSZ-100 was converted to the $NH_4^+$ form of SSZ-100 by heating the material in an aqueous solution of $NH_4NO_3$ (typically, 1 g of $NH_4NO_3$/1 g of SSZ-100 in 20 mL of deionized $H_2O$) at 90° C. for 2-3 hours. The mixture was then filtered and the step was repeated as many times as desired (usually done 2-3 times). After filtration, the obtained $NH_4^+$-exchanged product was washed with deionized water and air dried. The $NH_4^+$ form of SSZ-100 can be converted to the H form by calcination to 540° C.

Example 5

Constraint Index Test

The H form of SSZ-100 prepared per Example 4 was pelletized at 4 kpsi, crushed and granulated to 20-40 mesh. A 0.6 g sample of the granulated material was calcined in air at 540° C. for 4 hours and cooled in a desiccator to ensure dryness. Then, 0.47 g of material was packed into a ¼ inch stainless steel tube with alundum on both sides of the molecular sieve bed. A furnace (Applied Test Systems, Inc.) was used to heat the reactor tube. Nitrogen was introduced into the reactor tube at 9.4 mL/min and at atmospheric pressure. The reactor was heated to about 800° F. (427° C.), and a 50/50 feed of n-hexane and 3-methylpentane is introduced into the reactor at a rate of 8 μL/min. The feed was delivered by an ISCO pump. Direct sampling into a GC began after 15 minutes of feed introduction. Test data results after 15 minutes on stream (800° F.) are presented in Table 8.

TABLE 8

Constraint Index Test Results

| | |
|---|---|
| n-Hexane Conversion (%) | 11.2 |
| 3-MP Conversion (%) | 0.3 |
| Feed Conversion (%) | 5.7 |
| Constraint Index (excluding 2-MP) | 35.29 |
| Constraint Index (including 2-MP) | 63.66 |

MP = methylpentane

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. In a process for separating gases using a membrane containing a molecular sieve, the improvement comprising using as the molecular sieve a molecular sieve having a mole ratio of at least 10 of (1) at least one oxide of at least one tetravalent element to (2) one or more oxides selected from the group consisting of trivalent elements, pentavalent elements, and mixtures thereof, and having, in its calcined form, an X-ray diffraction substantially as shown in the following Table:

| 2-Theta | d-Spacing, nm | Relative Intensity |
|---|---|---|
| 8.48 ± 0.20 | 1.041 | VS |
| 8.98 ± 0.20 | 0.984 | VS |
| 10.04 ± 0.20 | 0.880 | S |
| 12.38 ± 0.20 | 0.714 | W |
| 14.17 ± 0.20 | 0.625 | W |
| 15.85 ± 0.20 | 0.559 | S |
| 17.07 ± 0.20 | 0.519 | W |
| 17.64 ± 0.20 | 0.503 | M |
| 18.68 ± 0.20 | 0.475 | S |
| 19.44 ± 0.20 | 0.456 | W |
| 19.78 ± 0.20 | 0.449 | M |
| 19.98 ± 0.20 | 0.444 | S |
| 20.22 ± 0.20 | 0.439 | W |
| 21.30 ± 0.20 | 0.417 | W |
| 22.80 ± 0.20 | 0.390 | M |
| 23.06 ± 0.20 | 0.385 | M |
| 24.29 ± 0.20 | 0.366 | W |
| 24.99 ± 0.20 | 0.356 | VS. |

2. The process of claim 1, wherein the molecular sieve has a mole ratio of at least 10 of (1) silicon oxide to (2) an oxide selected from boron oxide, aluminum oxide, gallium oxide, indium oxide, iron oxide, and mixtures thereof.

3. A process for the production of light olefins from a feedstock comprising an oxygenate or mixture of oxygenates, the process comprising reacting the feedstock at effective conditions over a catalyst comprising a molecular sieve having a mole ratio of at least 10 of (1) at least one oxide of at least one tetravalent element to (2) one or more oxides selected from the group consisting of trivalent elements, pentavalent elements, and mixtures thereof, and having, in its calcined form, an X-ray diffraction pattern substantially as shown in the following Table:

| 2-Theta | d-Spacing, nm | Relative Intensity |
| --- | --- | --- |
| 8.48 ± 0.20 | 1.041 | VS |
| 8.98 ± 0.20 | 0.984 | VS |
| 10.04 ± 0.20 | 0.880 | S |
| 12.38 ± 0.20 | 0.714 | W |
| 14.17 ± 0.20 | 0.625 | W |
| 15.85 ± 0.20 | 0.559 | S |
| 17.07 ± 0.20 | 0.519 | W |
| 17.64 ± 0.20 | 0.503 | M |
| 18.68 ± 0.20 | 0.475 | S |
| 19.44 ± 0.20 | 0.456 | W |
| 19.78 ± 0.20 | 0.449 | M |
| 19.98 ± 0.20 | 0.444 | S |
| 20.22 ± 0.20 | 0.439 | W |
| 21.30 ± 0.20 | 0.417 | W |
| 22.80 ± 0.20 | 0.390 | M |
| 23.06 ± 0.20 | 0.385 | M |
| 24.29 ± 0.20 | 0.366 | W |
| 24.99 ± 0.20 | 0.356 | VS. |

4. The process of claim 3, wherein the molecular sieve has a mole ratio of at least 10 of (1) silicon oxide to (2) an oxide selected from boron oxide, aluminum oxide, gallium oxide, indium oxide, iron oxide, and mixtures thereof.

5. The process of claim 3, wherein the light olefins are ethylene, propylene, butylene, or mixtures thereof.

6. The process of claim 5, wherein the light olefin is ethylene.

7. The process of claim 3, wherein the oxygenate is methanol, dimethyl ether, or a mixture thereof.

8. The process of claim 7, wherein the oxygenate is methanol.

9. A process for producing methylamine or dimethylamine comprising reacting methanol, dimethyl ether, or a mixture thereof, and ammonia in the gaseous phase in the presence of a catalyst comprising a molecular sieve having a mole ratio of at least 10 of (1) at least one oxide of at least one tetravalent element to (2) one or more oxides selected from the group consisting of trivalent elements, pentavalent elements, and mixtures thereof, and having, in its calcined form, an X-ray diffraction pattern substantially as shown in the following Table:

| 2-Theta | d-Spacing, nm | Relative Intensity |
| --- | --- | --- |
| 8.48 ± 0.20 | 1.041 | VS |
| 8.98 ± 0.20 | 0.984 | VS |
| 10.04 ± 0.20 | 0.880 | S |
| 12.38 ± 0.20 | 0.714 | W |
| 14.17 ± 0.20 | 0.625 | W |
| 15.85 ± 0.20 | 0.559 | S |
| 17.07 ± 0.20 | 0.519 | W |
| 17.64 ± 0.20 | 0.503 | M |
| 18.68 ± 0.20 | 0.475 | S |
| 19.44 ± 0.20 | 0.456 | W |
| 19.78 ± 0.20 | 0.449 | M |
| 19.98 ± 0.20 | 0.444 | S |
| 20.22 ± 0.20 | 0.439 | W |
| 21.30 ± 0.20 | 0.417 | W |
| 22.80 ± 0.20 | 0.390 | M |
| 23.06 ± 0.20 | 0.385 | M |
| 24.29 ± 0.20 | 0.366 | W |
| 24.99 ± 0.20 | 0.356 | VS. |

10. The process of claim 9, wherein the molecular sieve has a mole ratio of at least 10 of (1) silicon oxide to (2) an oxide selected from boron oxide, aluminum oxide, gallium oxide, indium oxide, iron oxide, and mixtures thereof.

11. The process of claim 9, wherein the methanol, dimethyl ether, or mixture thereof, and ammonia are present in amounts sufficient to provide a carbon/nitrogen ratio from 0.2 to 1.5.

12. The process of claim 9, conducted at a temperature of from 250° C. to 450° C.

13. A process for the reduction of oxides of nitrogen contained in a gas stream wherein the process comprises contacting the gas stream with a molecular sieve having a mole ratio of at least 10 of (1) at least one oxide of at least one tetravalent element to (2) one or more oxides selected from the group consisting of trivalent elements, pentavalent elements, and mixtures thereof, and having, in its calcined form, an X-ray diffraction pattern substantially as shown in the following Table:

| 2-Theta | d-Spacing, nm | Relative Intensity |
| --- | --- | --- |
| 8.48 ± 0.20 | 1.041 | VS |
| 8.98 ± 0.20 | 0.984 | VS |
| 10.04 ± 0.20 | 0.880 | S |
| 12.38 ± 0.20 | 0.714 | W |
| 14.17 ± 0.20 | 0.625 | W |
| 15.85 ± 0.20 | 0.559 | S |
| 17.07 ± 0.20 | 0.519 | W |
| 17.64 ± 0.20 | 0.503 | M |
| 18.68 ± 0.20 | 0.475 | S |
| 19.44 ± 0.20 | 0.456 | W |
| 19.78 ± 0.20 | 0.449 | M |
| 19.98 ± 0.20 | 0.444 | S |
| 20.22 ± 0.20 | 0.439 | W |
| 21.30 ± 0.20 | 0.417 | W |
| 22.80 ± 0.20 | 0.390 | M |
| 23.06 ± 0.20 | 0.385 | M |
| 24.29 ± 0.20 | 0.366 | W |
| 24.99 ± 0.20 | 0.356 | VS. |

14. The process of claim 1, wherein the molecular sieve has a mole ratio of at least 10 of (1) silicon oxide to (2) an oxide selected from boron oxide, aluminum oxide, gallium oxide, indium oxide, iron oxide, and mixtures thereof.

15. The process of claim 13, conducted in the presence of oxygen.

16. The process of claim 13, wherein the molecular sieve contains a metal or metal ions capable of catalyzing the reduction of the oxides of nitrogen.

17. The process of claim 16, wherein the metal is lanthanum, chromium, manganese, iron, cobalt, rhodium, nickel, palladium, platinum, copper, zinc, or mixtures thereof.

18. The process of claim 13, wherein the gas stream is the exhaust stream of an internal combustion engine.

19. A process for treating a cold-start engine exhaust gas stream containing hydrocarbons and other pollutants consisting of flowing the engine exhaust gas stream over a molecular sieve bed which preferentially adsorbs the hydrocarbons over water to provide a first exhaust stream, and flowing the first exhaust gas stream over a catalyst to convert any residual hydrocarbons and other pollutants contained in the first exhaust gas stream to innocuous products and provide a treated exhaust stream and discharging the treated exhaust stream into the atmosphere, the molecular sieve bed comprising a molecular sieve having a mole ratio of at least 10 of (1) at least one oxide of at least one tetravalent element to (2) one or more oxides selected from the group consisting of trivalent elements, pentavalent elements, and mixtures thereof, and having, in its calcined form, an X-ray diffraction pattern substantially as shown in the following Table:

| 2-Theta | d-Spacing, nm | Relative Intensity |
|---|---|---|
| 8.48 ± 0.20 | 1.041 | VS |
| 8.98 ± 0.20 | 0.984 | VS |
| 10.04 ± 0.20 | 0.880 | S |
| 12.38 ± 0.20 | 0.714 | W |
| 14.17 ± 0.20 | 0.625 | W |
| 15.85 ± 0.20 | 0.559 | S |
| 17.07 ± 0.20 | 0.519 | W |
| 17.64 ± 0.20 | 0.503 | M |
| 18.68 ± 0.20 | 0.475 | S |
| 19.44 ± 0.20 | 0.456 | W |
| 19.78 ± 0.20 | 0.449 | M |
| 19.98 ± 0.20 | 0.444 | S |
| 20.22 ± 0.20 | 0.439 | W |
| 21.30 ± 0.20 | 0.417 | W |
| 22.80 ± 0.20 | 0.390 | M |
| 23.06 ± 0.20 | 0.385 | M |
| 24.29 ± 0.20 | 0.366 | W |
| 24.99 ± 0.20 | 0.356 | VS. |

20. The process of claim 19, wherein the molecular sieve has a mole ratio of at least 10 of (1) silicon oxide to (2) an oxide selected from boron oxide, aluminum oxide, gallium oxide, indium oxide, iron oxide, and mixtures thereof.

21. The process of claim 19, wherein the engine is an internal combustion engine.

22. The process of claim 21, wherein the internal combustion engine is an automobile engine.

23. The process of claim 19, wherein the engine is fueled by a hydrocarbon fuel.

24. The process of claim 19, wherein the molecular sieve has deposited on it a metal selected from the group consisting of ruthenium, rhodium, palladium, platinum, and mixtures thereof.

25. The process of claim 24, wherein the metal is palladium, platinum, or a mixture thereof.

* * * * *